United States Patent
Kamon

(10) Patent No.: US 12,293,570 B2
(45) Date of Patent: May 6, 2025

(54) MEDICAL IMAGE LEARNING METHOD AND MEDICAL IMAGE PROCESSING DEVICE

(71) Applicant: FUJIFILM Corporation, Tokyo (JP)

(72) Inventor: Shumpei Kamon, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 518 days.

(21) Appl. No.: 17/815,926

(22) Filed: Jul. 28, 2022

(65) Prior Publication Data
US 2023/0029934 A1 Feb. 2, 2023

(30) Foreign Application Priority Data
Jul. 29, 2021 (JP) .................. 2021-124718

(51) Int. Cl.
*G06V 10/774* (2022.01)
*G06T 7/00* (2017.01)
(Continued)

(52) U.S. Cl.
CPC .......... *G06V 10/774* (2022.01); *G06T 7/0014* (2013.01); *G06V 10/25* (2022.01); *G06V 10/40* (2022.01); *G16H 30/20* (2018.01); *G16H 30/40* (2018.01); *G06T 2207/10068* (2013.01); *G06T 2207/20081* (2013.01); *G06T 2207/30096* (2013.01); *G06V 2201/03* (2022.01)

(58) Field of Classification Search
CPC ...... G06V 10/774; G06V 10/25; G06V 10/40; G06V 2201/03; G06V 10/776; G06T 7/0014; G06T 2207/10068; G06T 2207/20081; G06T 2207/30096; G06T 7/0012; G16H 30/20; G16H 30/40; G16H 50/20; G16H 50/70

USPC ......................................... 382/128
See application file for complete search history.

(56) References Cited

U.S. PATENT DOCUMENTS

| 2019/0198156 A1 | 6/2019 | Madani et al. |
| 2023/0298445 A1* | 9/2023 | Liu .................. G06V 10/82 348/143 |

FOREIGN PATENT DOCUMENTS

| JP | 2020086698 A | * | 6/2020 |
| JP | 2021058464 A | * | 4/2021 |

OTHER PUBLICATIONS

Toru Nagamura et al., "Pneumonia Detection Using Anomaly Detection by U-net", Multimedia, Distributed, Cooperative and Mobile (DICOMO2020) Symposium, vol. 2020, No. 1, Jun. 24, 2020, pp. 526-533.

(Continued)

*Primary Examiner* — Juan A Torres
(74) *Attorney, Agent, or Firm* — Studebaker Brackett PLLC

(57) ABSTRACT

A trained first model is generated through first learning using a first learning image group constituted of a normal image which is a medical image having no region of interest. An input image group including at least the medical image different from the first learning image group is input to the trained first model, and abnormality detection is performed. The extracted image used for learning to prevent erroneous recognition is sorted according to a result of the abnormality detection, and second learning using a second learning image group including at least the extracted image is performed. A second model that detects the region of interest is generated through the second learning.

13 Claims, 11 Drawing Sheets

(51) Int. Cl.
*G06V 10/25* (2022.01)
*G06V 10/40* (2022.01)
*G16H 30/20* (2018.01)
*G16H 30/40* (2018.01)

(56) References Cited

OTHER PUBLICATIONS

Haichao Cao et al., "A Two-Stage Convolutional Neural Networks for Lung Nodule Detection", IEEE Journal of Biomedical and Health Informatics, vol. 24, No. 7, Jan. 3, 2020, pp. 2006-2015.
An Office Action; "Notice of Reasons for Refusal," mailed by the Japanese Patent Office on Mar. 4, 2025, which corresponds to Japanese Patent Application No. 2021-124718 and is related to U.S. Appl. No. 17/815,926; with English language translation.

\* cited by examiner

FIG. 6
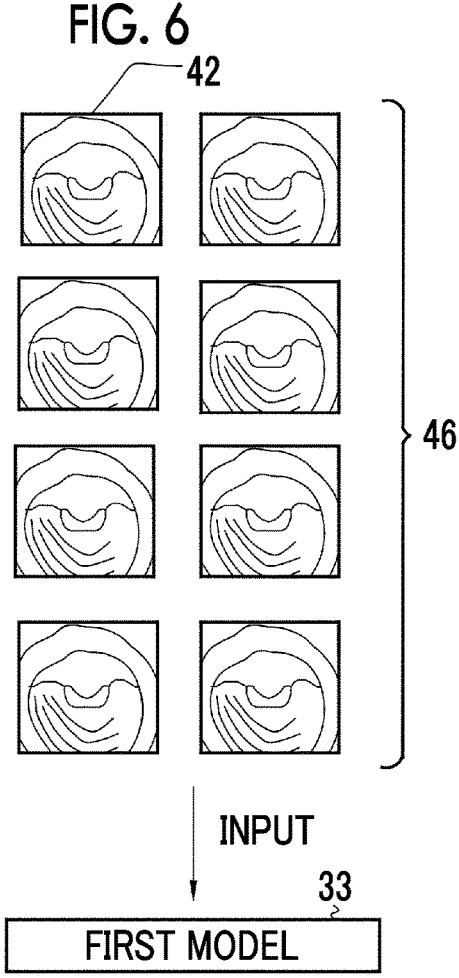
INPUT
FIRST MODEL — 33
DETERMINED TO BE NORMAL
DETERMINED TO BE ABNORMAL
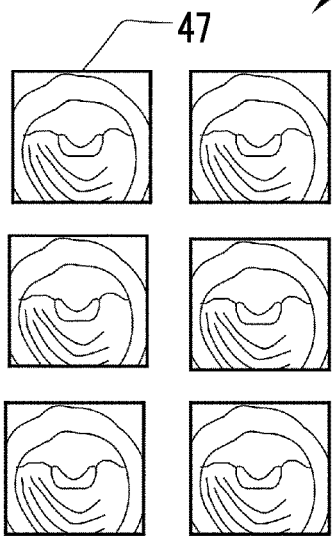
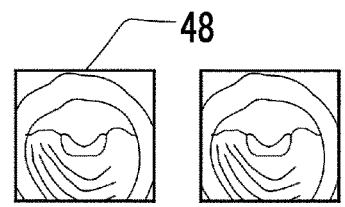

FIG. 8

|  | FIRST SORTING | SECOND SORTING |
|---|---|---|
| INPUT IMAGE | NORMAL IMAGE | ABNORMAL IMAGE |
| RESULT OF ABNORMALITY DETECTION: NORMAL | NON-EXTRACTED NORMAL IMAGE | EXTRACTED ABNORMAL IMAGE |
| RESULT OF ABNORMALITY DETECTION: ABNORMAL | EXTRACTED NORMAL IMAGE | NON-EXTRACTED ABNORMAL IMAGE |

FIG. 9

| IMAGE | FIRST SORTING | | | SECOND SORTING | | |
|---|---|---|---|---|---|---|
| | A | B | C | D | E | F |
| RESULT OF ABNORMALITY DETECTION | NORMAL | ABNORMAL | ABNORMAL | NORMAL | ABNORMAL | ABNORMAL |
| SORTING RESULT | NON-EXTRACTED | EXTRACTED | EXTRACTED | EXTRACTED | NON-EXTRACTED | NON-EXTRACTED |
| PRESENCE OR ABSENCE AND TYPE OF ABNORMALITY | NONE | TREATED MARK | NONE | TUMOR/SMALL | BLEEDING/SMALL | TUMOR/LARGE |
| DEGREE OF ABNORMALITY | 0 | 6 | 3 | 2 | 5 | 7 |

FIG. 12
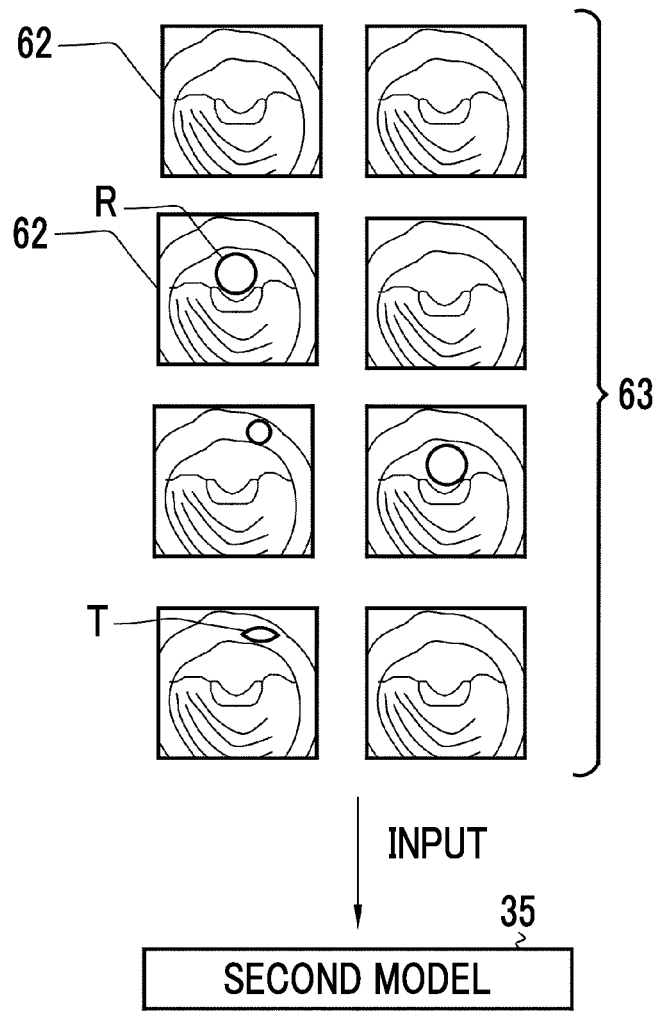
INPUT
SECOND MODEL 35
DETECT REGION OF INTEREST
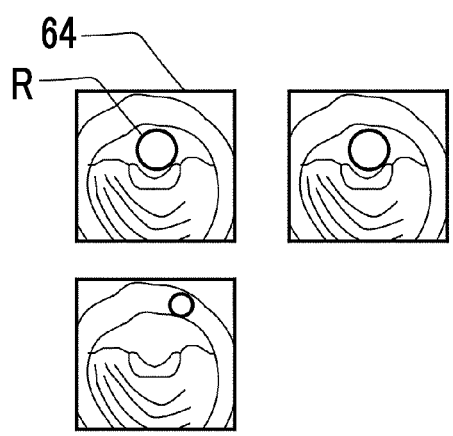

MEDICAL IMAGE LEARNING METHOD AND MEDICAL IMAGE PROCESSING DEVICE

CROSS-REFERENCE TO RELATED APPLICATIONS

This application claims priority under 35 U.S.C § 119(a) to Japanese Patent Application No. 2021-124718 filed on 29 Jul. 2021. The above application is hereby expressly incorporated by reference, in its entirety, into the present application.

BACKGROUND OF THE INVENTION

1. Field of the Invention

The present invention relates to a medical image learning method and a medical image processing device.

2. Description of the Related Art

A case of learning to detect a region of interest including a lesion from a medical image is assumed. For accurate learning, it is necessary to collect not only images including the regions of interest but also images not including the regions of interest so as to cover various variations, and the recording of an examination motion picture makes it possible to collect a large number of frame images.

However, the use of a large number of collected frame images as they are as learning data leads to inefficiency in learning because the motion picture frame during the examination includes many images that are not useful for learning. For example, there arises a problem that a large number of similar images are collected and a large number of images not including the regions of interest are collected. Although the similar images contribute less to learning because there is no difference in the amount of information between the similar images even in a case where a large number of similar images exist, there is a tendency to excessively collect similar images particularly because frames not including the regions of interest are included most of the time during the examination. The excessive collection of images not including the regions of interest leads to a class imbalance problem, which is not desirable and causes pressure on a recording storage. A method is conceivable in which a large number of images are collected and then the images are randomly reduced in order to avoid pressure on the storage, but there is a concern that the accuracy may decrease because there is also a probability that image data useful for learning may be reduced and may not be used for learning.

JP2020-86698A describes that a diagnostic result image obtained by extracting an abnormal part from a medical image is generated by using an abnormal part detector that outputs an abnormal part extraction image and a peculiar part estimator that outputs a peculiar part estimation image. JP2021-58464A describes a first trained model that is trained with identification information corresponding to polyp and a second trained model that is trained with identification information corresponding to a structure except for the polyp output by the first trained model, in which the second trained model determines the identification information corresponding to the structure except for the polyp.

SUMMARY OF THE INVENTION

In JP2020-86698A, the trained abnormal part detector and the trained peculiar part estimator are used to detect a medical image having the abnormal part, but there is no description that the abnormal part is distinguished from an abnormality that is not a lesion, such as a treated mark or a blister. In JP2021-58464A, although the second model is trained with information not corresponding to the lesion, which is output by the first model trained with information corresponding to the lesion, and the trained second model receives images, as an input, to sort the images according to a characteristic, there is a description for preventing erroneous detection of a normal image that is near the boundary in the identification and that is easily detected as a lesion, but there is no description for preventing non-detection of a difficult-to-detect lesion image. There is also no description for preventing bias in the content of learning and stabilizing learning. It is desirable to be able to sort abnormal images for preventing erroneous non-detection or erroneous detection from a large number of frame images acquired by motion picture imaging by accurately learning the region of interest, such as a lesion, on the basis of the above points.

An object of the present invention is to provide a medical image learning method and a medical image processing device that generate a trained model which reduces the load on a recording storage and which detects a region of interest with high accuracy in learning using a large number of collected frame images.

There is provided a medical image learning method according to an aspect of the present invention comprising: performing abnormality detection in response to an input of an input image group to a first model generated through first learning using a first learning image group constituted of a normal image which is a medical image having no region of interest, the input image group including at least the medical image different from the first learning image group; performing sorting of an extracted image, which is used for learning to prevent erroneous recognition, according to a result of the abnormality detection; and generating a second model, which detects the region of interest, through second learning using a second learning image group including at least the sorted extracted image, out of the input image group.

It is preferable that each medical image of the input first learning image group is generated or restored in the first learning.

It is preferable that the sorting performed for the input image group consisting of the normal image is first sorting, and the medical image determined to be abnormal as the result of the abnormality detection is sorted into the extracted image through the first sorting.

It is preferable that the sorting performed for the input image group consisting of an abnormal image is second sorting, and the medical image determined to be normal as the result of the abnormality detection is sorted into the extracted image through the second sorting.

It is preferable that the sorting performed for the input image group consisting of the normal image is first sorting, the medical image determined to be abnormal as the result of the abnormality detection is sorted into the extracted image through the first sorting, the sorting performed for the input image group consisting of an abnormal image is second sorting, the medical image determined to be normal as the result of the abnormality detection is sorted into the extracted image through the second sorting, there are a case where the input image group consists of the normal image and a case where the input image group consists of the abnormal image, and the first model switches between the first sorting and the second sorting depending on a type of the input image group.

It is preferable that the second learning image group includes the extracted image and the medical image different from the extracted image.

It is preferable that a degree of abnormality of each medical image of the input image group is evaluated through the abnormality detection, and that the second model is generated through the second learning using the second learning image group weighted on each medical image according to the degree of abnormality.

It is preferable that in the weighting, weight is set small for an extracted normal image and an extracted abnormal image, which are the extracted images, and weight is set large for a non-extracted normal image and a non-extracted abnormal image, which are not the extracted images.

It is preferable that the first model is an autoencoder, and the first model learns autoencoding and calculates a reference intermediate feature amount of the normal image, in the first learning, acquires an autoencoded image and an intermediate feature amount on the basis of each medical image of the input image group input to the first model, and performs the abnormality detection by using at least one of a restoration error obtained by comparing an image before the autoencoding with the autoencoded image or a comparison result between the reference intermediate feature amount and the intermediate feature amount.

It is preferable that the first model is a GAN, and performs the abnormality detection by using at least one of a trained discriminator or a trained generator.

It is preferable that the first model learns image interpolation through the first learning, makes each medical image constituting the input image group, which is input to the first model, deficient and interpolates the deficiency by using a reference calculated through the first learning, and performs the abnormality detection by using a restoration error calculated by comparing the medical image before the deficiency with the medical image after the interpolation.

There is provided a medical image processing device according to another aspect of the prevent invention comprising a processor, in which the processor performs abnormality detection in response to an input of an input image group to a first model generated through first learning using a first learning image group constituted of a normal image which is a medical image having no region of interest, the input image group including at least the medical image different from the first learning image group, performs sorting of an extracted image, which is used for learning to prevent erroneous recognition, according to a result of the abnormality detection, and generates a second model, which detects the region of interest, through second learning using a second learning image group including at least the sorted extracted image, out of the input image group.

A trained model that reduces the load on a recording storage and detects a region of interest with high accuracy can be generated through learning using a large number of collected frame images.

BRIEF DESCRIPTION OF THE DRAWINGS

FIG. 6 is a diagram illustrating first sorting for sorting an extracted image from a normal image.

FIG. 8 is a diagram illustrating an input and abnormality detection in the first sorting and the second sorting.

FIG. 9 is a diagram illustrating a specific example in which a degree of abnormality is evaluated for an image after the sorting.

FIG. 12 is a diagram illustrating a function of a trained second model.

DESCRIPTION OF THE PREFERRED EMBODIMENTS

Figure 1:
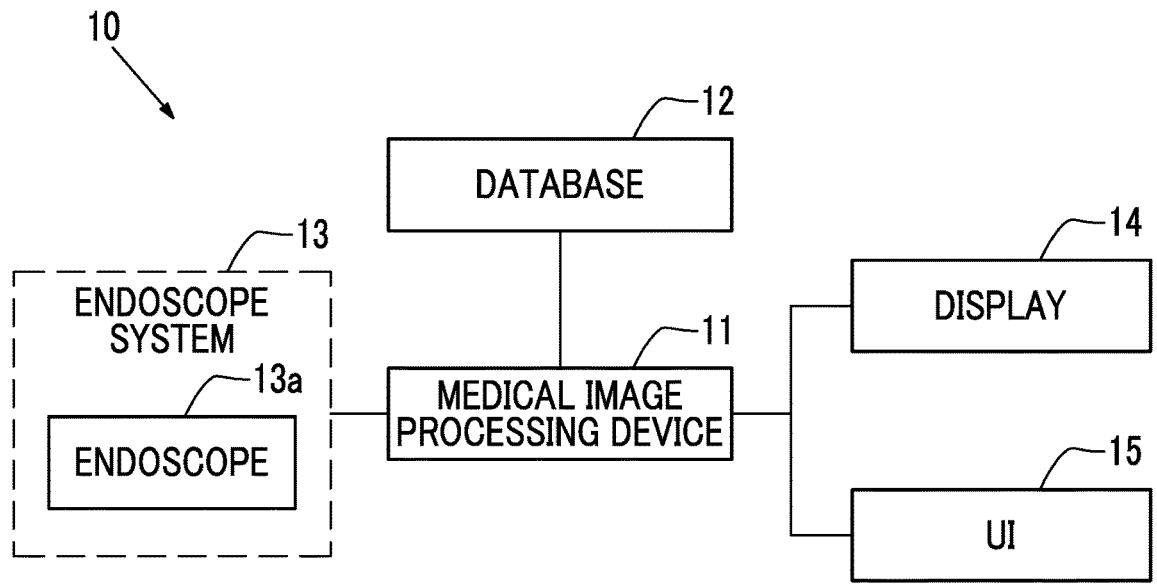
FIG. 1 is a diagram illustrating a connection device of a medical image processing device.

FIG. 1 is a diagram showing a configuration example of a medical image processing system 10 that realizes a medical image learning method according to the embodiment of the present invention. The medical image processing system 10 includes a medical image processing device 11, a database 12, an endoscope system 13 having an endoscope 13a, a display 14, and a user interface 15. The medical image processing device 11 is electrically connected to the database 12, the endoscope system 13, the display 14, and the user interface 15.

The database 12 is a device that stores acquired images and that can transmit and receive data to and from the medical image processing device 11, and may be a recording medium, such as a Universal Serial Bus (USB) or a hard disc drive (HDD). The medical image processing device 11 acquires images captured in examination from the endoscope 13a constituting the endoscope system 13. The user interface 15 is an input device through which settings and the like to the medical image processing device 11 are input, and includes a keyboard, a mouse, and the like.

The database 12 stores frame images of an examination motion picture captured in endoscopy or the like. Unless otherwise specified in imaging, white light is used as illumination light, a video signal of a 60-frame image (60 frames per second (fps)) is acquired per second, and the imaging time is recorded. It is preferable to count the time in a unit of $1/100$ seconds in a case where the video signal is 60 fps.

Figure 2:
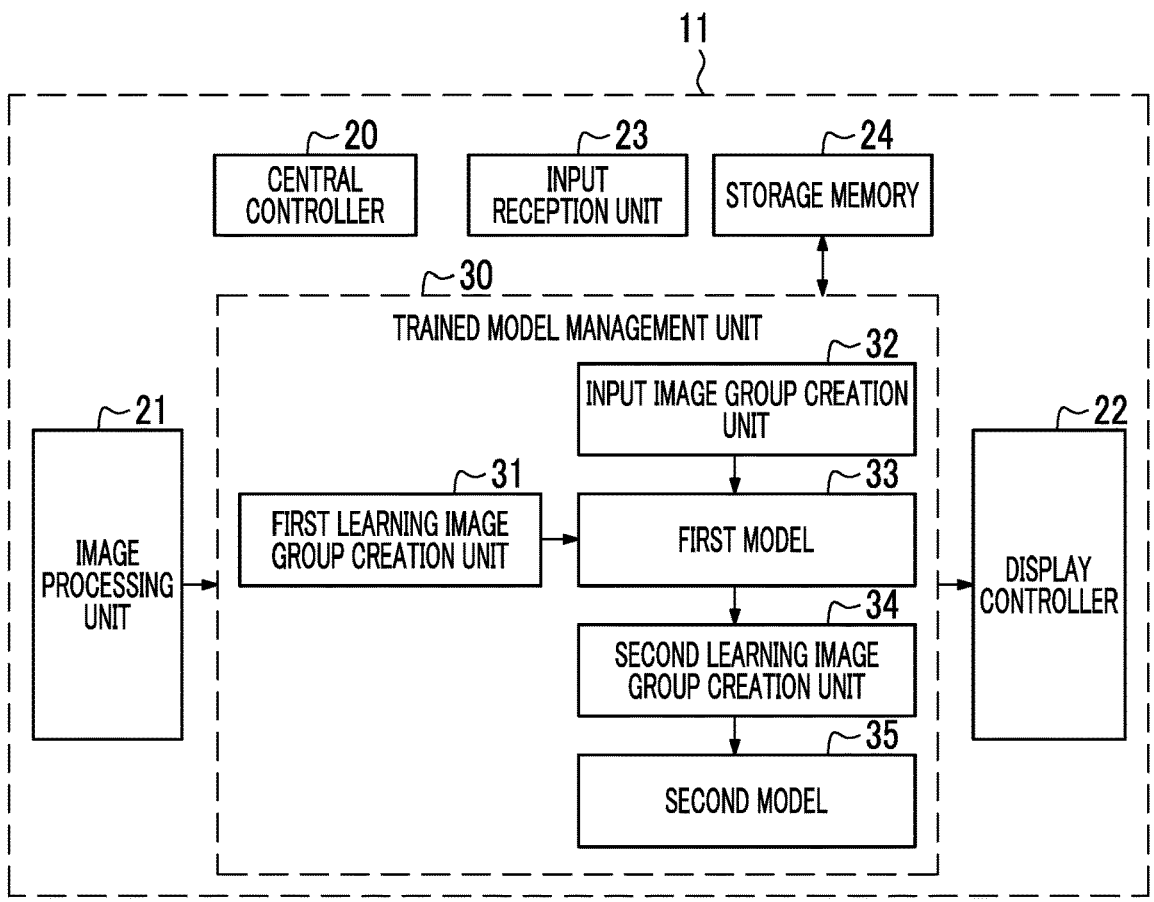
FIG. 2 is a block diagram showing a function of the medical image processing device.

As shown in FIG. 2, in the medical image processing device 11, a program in a program memory is operated by a central controller 20 constituted of a processor for image control, whereby the functions of an image processing unit 21, a display controller 22, an input reception unit 23, a storage memory 24, and a trained model management unit 30 are realized. In addition, the functions of a first learning image group creation unit 31, an input image group creation unit 32, a first model 33, a second learning image group creation unit 34, and a second model 35 are realized with the realization of the functions of the trained model management unit 30. The image processing unit 21 receives data, such as an image acquired by the endoscope system 13. The display controller 22 performs control for causing a display 14 to display a still picture or a motion picture. The input reception unit 23 is connected to the user interface 15. Although the storage memory 24 can realize a storage function independently, the storage memory 24 can transmit and receive data through the connection with the database 12. Further, in the medical image processing device 11, a program related to processing such as image processing is stored in the program memory (not shown). The first model 33 and the second model 35 are each computer algorithm consisting of neural networks that are trained through input learning data, and classify images and detect specific images according to the content of learning.

Figure 3:
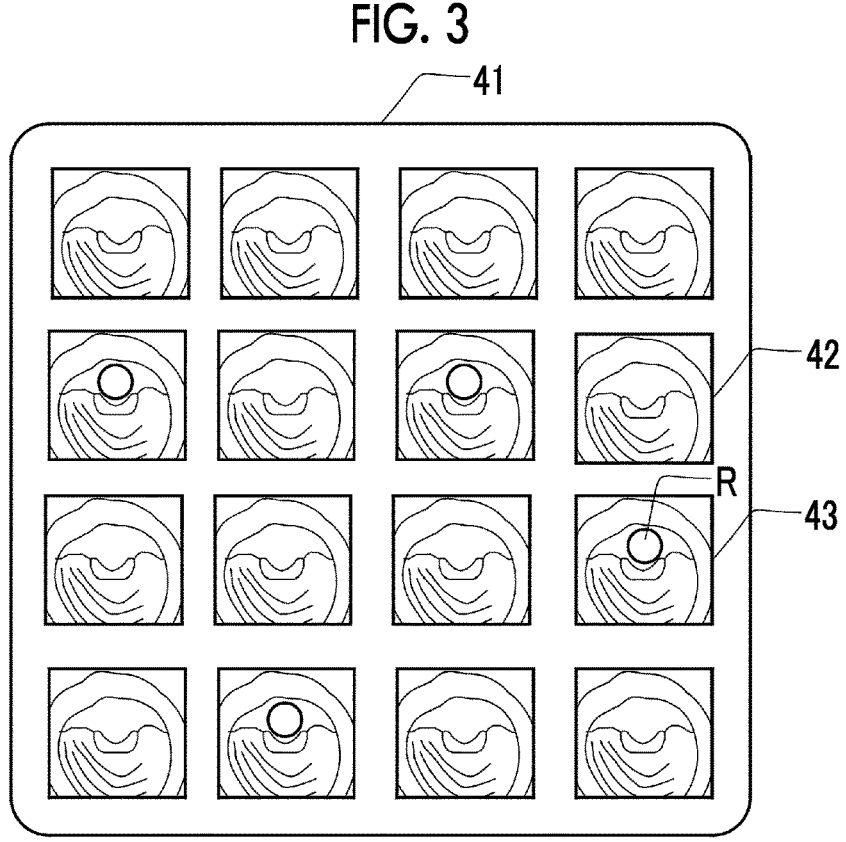
FIG. 3 is a diagram illustrating images stored in a database used for learning.

As shown in FIG. 3, the database 12 stores a large number of images as a stored image group 41. The stored image group 41 includes a normal image 42 having no region of interest R, such as a lesion, and an abnormal image 43 having the region of interest R, such as a lesion, as images used for the learning or input for the first model 33 and the second model 35. It is preferable that the normal image 42 and the abnormal image 43 can be easily distinguished from each other with a method other than visual identification of the image, such as tagging as to whether or not the region of interest R is present, because first learning through which the first model 33 is trained uses the normal image 42.

The trained model management unit 30 creates a trained first model 33 that performs abnormality detection, through the first learning using the normal image 42 taken out from the stored image group 41, and creates a trained second model 35 that detects the region of interest R, through the second learning using the result of the abnormality detection.

Figure 4:
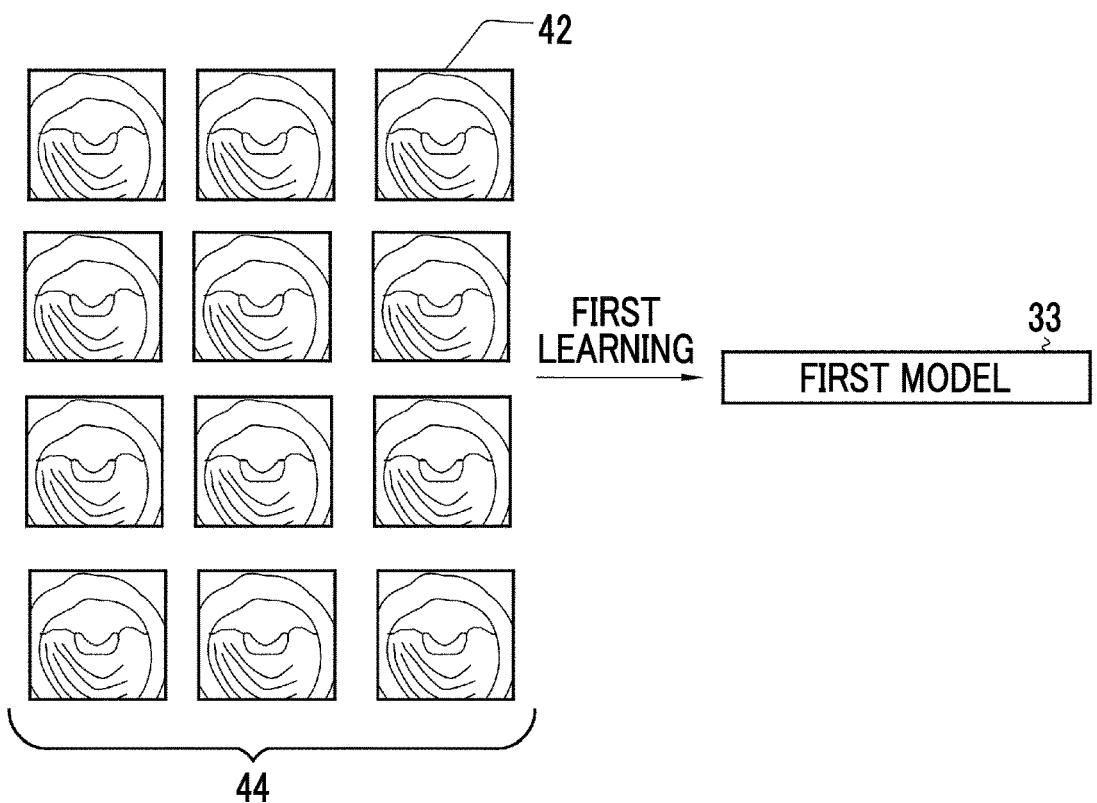
FIG. 4 is a diagram illustrating first learning in which a first learning image group is input to a first model.

As shown in FIG. 4, the first learning image group creation unit 31 acquires a plurality of normal images 42 from the stored image group 41 and creates a first learning image group 44 used for the first learning. Further, the first learning through which the first model 33 learns the first learning image group 44 and a reference in the determination of the abnormality detection is calculated is performed. With this, the first model 33 can acquire an extracted image that is highly likely to be useful for preventing erroneous recognition of the region of interest R in learning, through sorting performed using the abnormality detection with respect to the image input on the basis of the content of learning. The extracted image corresponds to, for example, an image that is at an identification boundary between the detection and non-detection of the region of interest R. The first learning image group 44 may include about one abnormal image 43 that can be compared with the normal image 42 with regard to the presence or absence of the region of interest R. The abnormality detection using the calculated reference has a plurality of patterns depending on the learning method in the first learning, and examples thereof include learning of an autoencoder, learning of generative adversarial network (GAN), or learning of image interpolation. Details of the learning method will be described later. Further, it is preferable that the first model 33 generates or restores the input image in the first learning.

Figure 5:
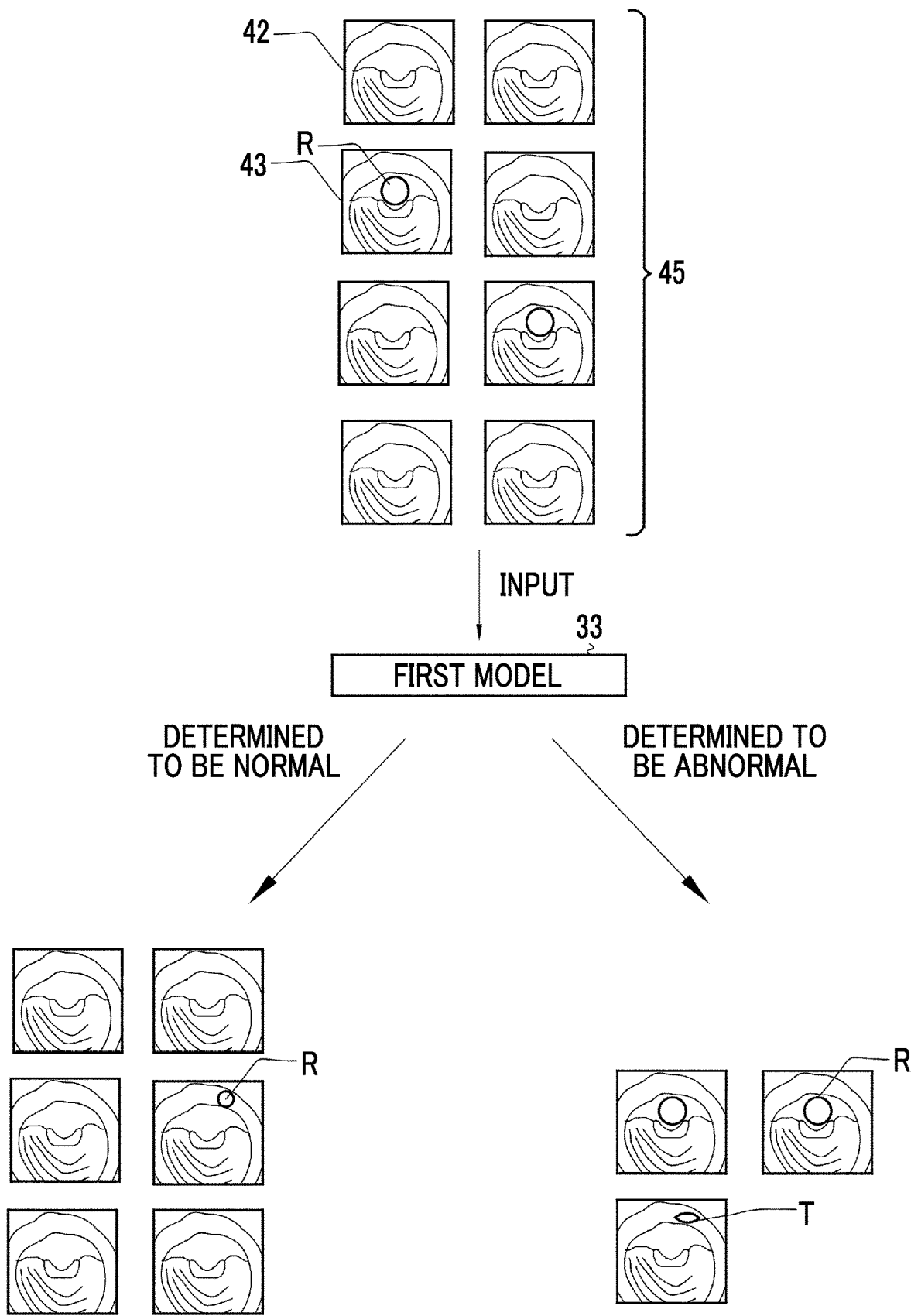
FIG. 5 is a diagram illustrating a function of a trained first model.

As shown in FIG. 5, whether the generation of the trained first model 33 capable of correctly performing the abnormality detection after the first learning is completed may be confirmed. Whether the input image is normal or abnormal is determined through the abnormality detection. An image that is highly likely not to include a lesion and does not have the region of interest R, which is close to the content of the first learning, is determined to be normal. In addition, an image that is highly likely to include a lesion and has the region of interest R, which is not close to the content of the first learning, is determined to be abnormal. Therefore, a confirmation image group 45 including at least one normal image 42 and at least one abnormal image 43 from the stored image group 41 is input to the trained first model 33, whereby the generation of the trained first model 33 can be confirmed on the basis of the determination result. However, since the abnormality detection is a determination using the first learning image group 44 as a reference, a treated mark T, a blister, or the like may be determined as an abnormal part, that is, an image that does not include the region of interest R may be determined to be abnormal, despite the normal image 42, or a minute lesion or the like may not be detected, that is, an image that has the region of interest R may be determined to be normal, despite the abnormal image 43. The treated mark T is a part where the lesion has been treated in the past.

The images useful for the second learning are sorted by using the abnormality detection performed by the generated trained first model 33. The second learning is learning to create a reference in the detection of the region of interest R for the second model. The trained first model 33 receives an input of an input image group consisting of the plurality of images included in the stored image group 41 to perform the abnormality detection, and performs sorting according to the result of the abnormality detection. The image sorted and acquired is an extracted image useful for preventing erroneous recognition in the identification of the region of interest R, and enables the second model to accurately detect the region of interest R through the second learning using the extracted image. The sorting includes first sorting for acquiring the extracted image through the input of the plurality of normal images 42 to the trained first model 33 and second sorting for acquiring the extracted image through the input of the plurality of abnormal images 43 to the trained first model 33. Further, an image that is not acquired as the extracted image through the sorting is a non-extracted image that is highly unlikely to be useful for preventing erroneous recognition.

In FIG. 6, a first input image group 46 consisting of the normal image 42 is created by the input image group creation unit 32, and the first sorting is performed and the extracted image is acquired. Most of the result of the abnormality detection of the first input image group 46 is determined to be normal because the normal image 42 does not include the region of interest R, but a small number of images having a large difference from the reference of the first model 33 are determined to be abnormal. The normal image 42 determined to be normal is a non-extracted normal image 47 which is the non-extracted image. Further, the normal image 42 determined to be abnormal is the extracted image, and is an extracted normal image 48 used for the second learning as the image useful for preventing erroneous detection of the region of interest R. In a case where the extracted normal image 48 is not sufficiently obtained in the abnormality detection of the first input image group 46, the first sorting is performed again by using the different normal image 42 from the stored image group 41. The first input image group 46 includes at least the normal image 42 that is not included in the first learning image group 44.

Figure 7:
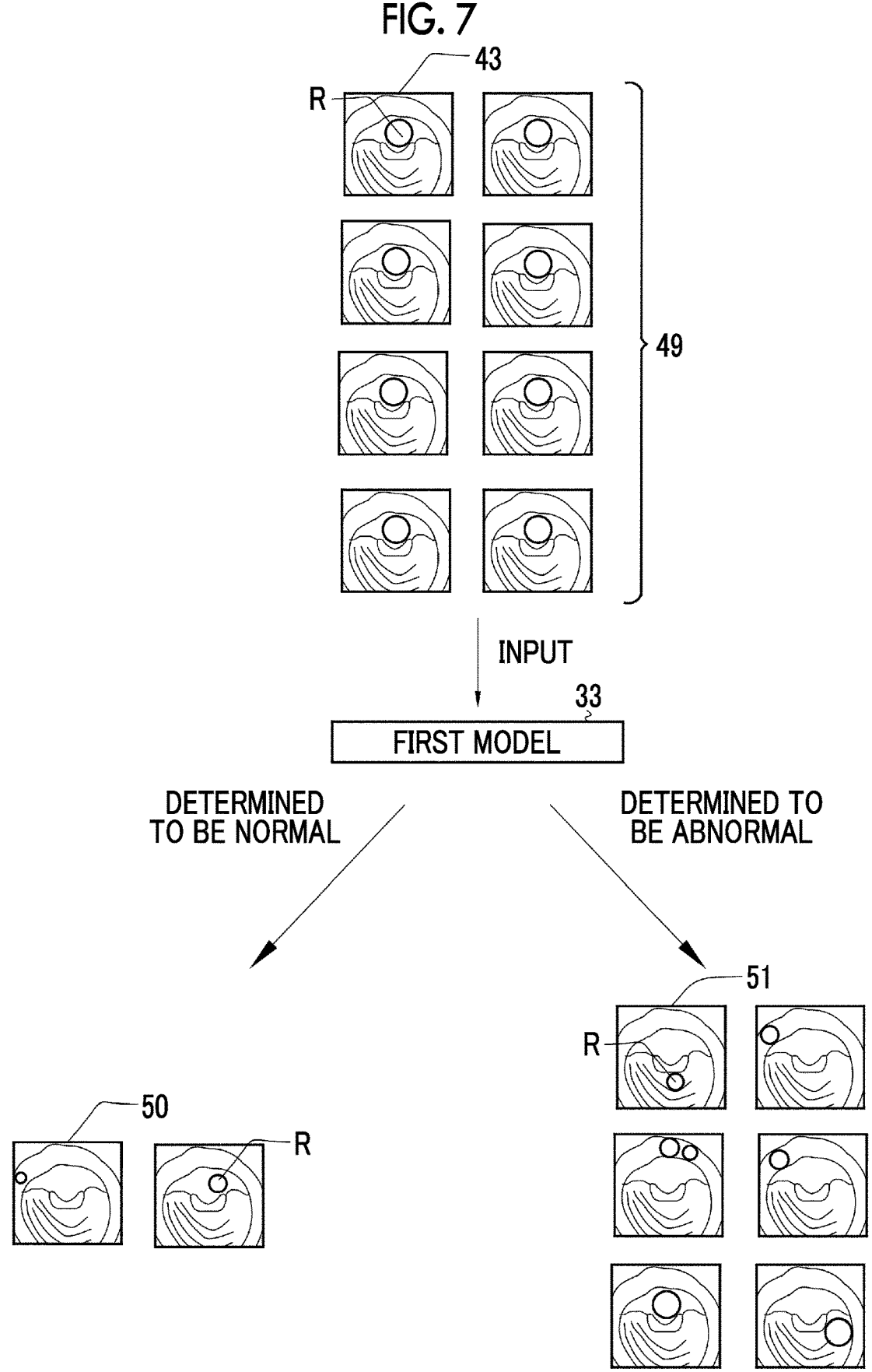
FIG. 7 is a diagram illustrating second sorting for sorting the extracted image from an abnormal image.

In FIG. 7, a second input image group 49 consisting of the abnormal image 43 is created by the input image group creation unit 32, and the second sorting is performed and the extracted image is acquired. Most of the result of the abnormality detection of the second input image group 49 is determined to be abnormal because the abnormal image 43 includes the region of interest R, but a small number of images having a small difference from the reference of the first model 33 are determined to be normal. The abnormal image 43 determined to be normal is the extracted image, and is an extracted abnormal image 50 used for the second learning as an image useful for preventing erroneous non-detection of the region of interest R. The abnormal image 43 determined to be abnormal is a non-extracted abnormal image 51 which is the non-extracted image. In a case where the extracted abnormal image 50 is not sufficiently obtained in the abnormality detection of the first input image group 46, the second sorting is performed again by using the different abnormal image 43 from the stored image group 41.

As shown in FIG. 8, four types of images can be acquired through the first sorting and the second sorting. The non-extracted normal image 47 and the extracted normal image 48 are obtained from the first sorting, and the non-extracted abnormal image 51 and the extracted abnormal image 50 are obtained from the second sorting. The input image group creation unit 32 creates an input image group of any one of the first input image group 46 or the second input image group 49 to be input to the first model, and the trained first model 33 switches the first sorting and the second sorting depending on the type of the input image group. In addition, at least one of the first sorting or the second sorting is performed for the sorting.

The trained first model 33 may evaluate the degree of abnormality of each image at the time of the sorting in which normality or abnormality is determined through the abnormality detection. The degree of abnormality is evaluated from the difference obtained by comparison with the reference of the first model using at least one or more items related to image information and an image feature amount in which a value varies clearly depending on the presence or absence and the size of the region of interest R. Examples of the items used for evaluation of the degree of abnormality include an average by density/tint, a histogram, a frequency distribution, an edge intensity distribution by an edge direction, a fractal dimension, a brightness distribution, and an average value of brightness. An image having a value close to the reference value of the first model is evaluated as a low degree of abnormality, and an image having a value not close to the reference value is evaluated as a high degree of abnormality. The second learning is performed with a learning method, such as weighting, by using the degree of abnormality.

The extracted image is stored automatically or through user operation, and is held as an image for learning. Only the extracted image, which is extracted through the sorting, is stored in the storage of each facility, such as the database 12 or the storage memory 24, and a large number of other non-extracted images are deleted, whereby the storage capacity can be saved. It is preferable to perform tagging or the like for discriminating that the extracted image to be stored is useful for learning to prevent erroneous recognition.

FIG. 9 is an example in which the difference from the reference of the first model is comprehensively evaluated as the degree of abnormality in 10 stages from 0 to 9 and is used for the second learning, in addition to the sorting result of the first sorting or the second sorting. A case where the degree of abnormality is evaluated for images A to C used for the first sorting and images D to F used for the second sorting will be described. The larger the difference is, the larger the numerical value of the degree of abnormality is, and a case where the degree of abnormality is 0 to 2 is determined to be normal and a case where the degree of abnormality is 3 to 9 is determined to be abnormal. For example, in the image A, there is no difference from the reference of the first model, and the degree of abnormality is 0. In the image B, there is a treated mark T, and the degree of abnormality is 6. In the image C, there is a shadowed part of illumination light, and the degree of abnormality is 3. In the image D, there is an inconspicuous small tumor, and the degree of abnormality is 2. In the image E, there is a small area of bleeding, and the degree of abnormality is 5. In the image F, there is a large tumor, and the degree of abnormality is 7. The larger the numerical value of the degree of abnormality is, the more likely there is a serious lesion, but the extracted normal image 48 including the treated mark or the like also has a high degree of abnormality, as described above. Therefore, it is preferable to perform the second learning by incorporating learning methods, such as weighting, in addition to the evaluation of the degree of abnormality.

A case where weighting is performed on the images constituting a second learning image group will be described. Since the extracted normal image 48 and the extracted abnormal image 50, which are useful for learning to prevent erroneous recognition, are rarely used for the determination and there is a concern that the accuracy may decrease in a case where the extracted normal image 48 and the extracted abnormal image 50 are treated in the same manner as the non-extracted normal image 47 or the non-extracted abnormal image 51, which is the non-extracted image, a difference in priority is given by weighting. For example, the extracted normal image 48 and the extracted abnormal image 50 are weighted with "a" (a>0), which is a value larger than 0, the non-extracted normal image 47 is weighted with "b", which is a value larger than a, and the non-extracted abnormal image 51 having the region of interest R is weighted with "c" (c≥b>a>0), which is the same value as or larger than b.

Figure 10:
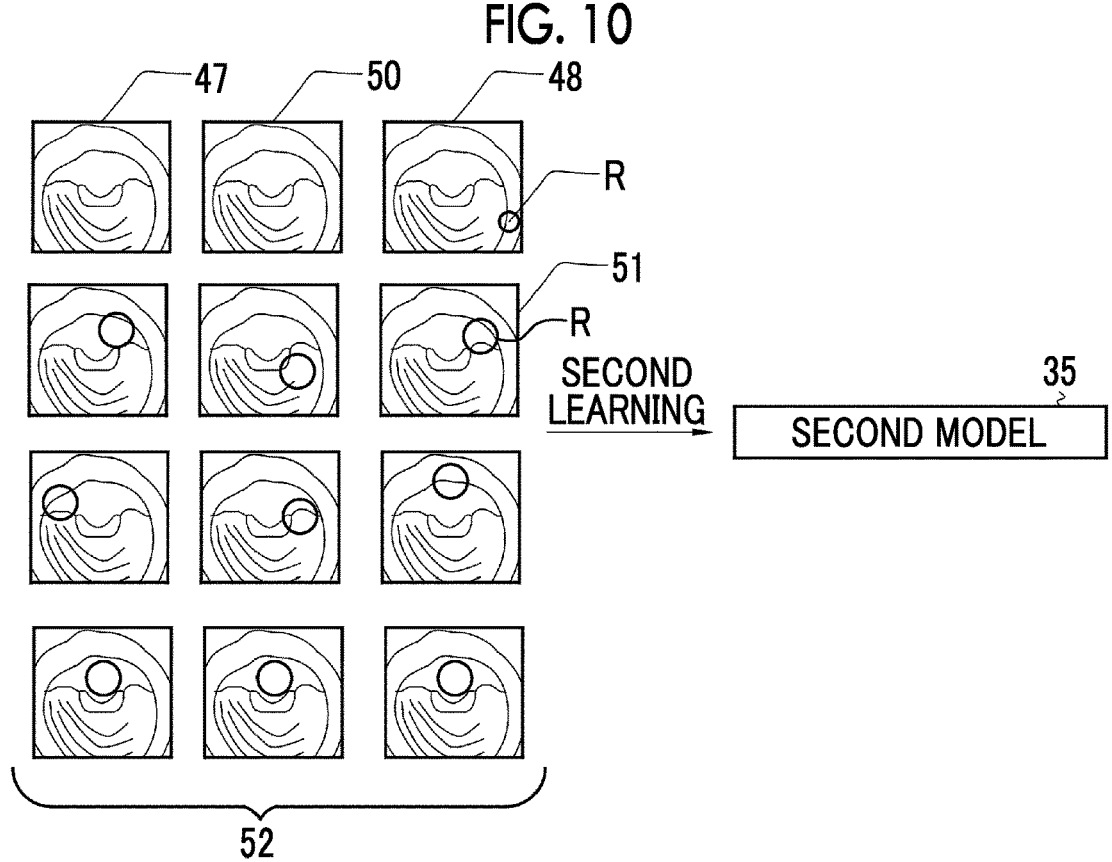
FIG. 10 is a diagram illustrating second learning in which a second learning image group is input to a second model.

As shown in FIG. 10, the second learning through which the second model 35 learns a second learning image group 52 will be described. The second learning image group 52 is constituted of the extracted normal image 48 and the extracted abnormal image 50, which are acquired through the first sorting and the second sorting, and the non-extracted abnormal image 51. Further, it is preferable that the non-extracted normal image 47 is also included randomly from a large number of acquired images, in order to compare the presence or absence of the region of interest R and prevent the instability of learning. For example, the non-extracted abnormal image 51 is made to mainly constitute the second learning image group 52, and the extracted normal image 48, the non-extracted normal image 47, and the extracted abnormal image 50, which are rarely used for the determination, are made to constitute the second learning image group 52 so as to be included in constant ratios with respect to the non-extracted abnormal image 51, and then the second model is trained therewith, whereby a trained second model 35 that detects the region of interest R is generated.

In the above description, the extracted image acquired through the sorting, the non-extracted normal image 47, and the non-extracted abnormal image 51 as the non-extracted images are adopted as the second learning image group 52, but the extracted image may be prepared in advance as the stored image group 41, and the normal image 42 or the abnormal image 43, which is highly unlikely to be useful for preventing erroneous recognition, may be used for the second learning as the non-extracted image.

Figure 11:
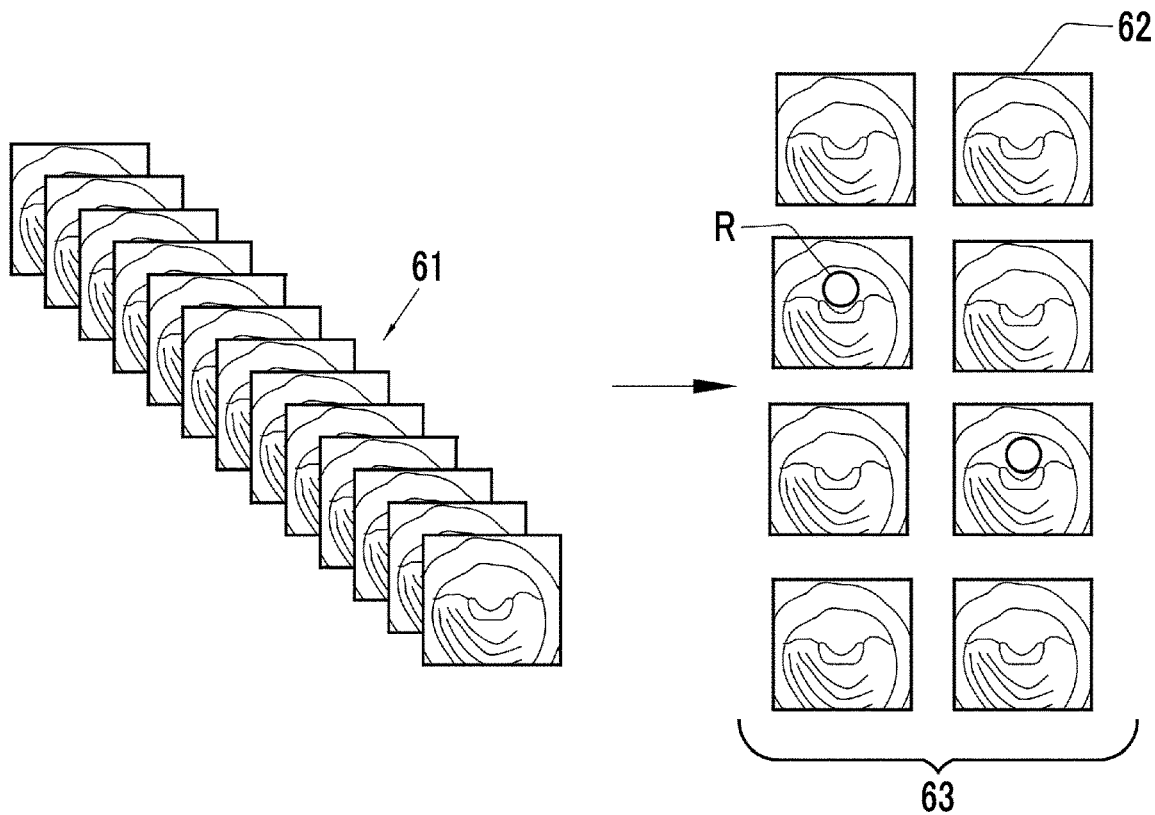
FIG. 11 is a diagram illustrating division of an examination motion picture for each frame.

The trained second model 35 detects the region of interest R for a large number of still pictures in which the examination motion picture is framed. Here, an endoscopy motion picture captured by the endoscope 13a will be described as an example. As shown in FIG. 11, the image processing unit 21 receives an examination motion picture 61 in which endoscopy using the endoscope 13a is recorded from the endoscope system 13 after the end of the endoscopy, and acquires an examination frame image group 63 consisting of a large number of examination frame images 62 in which the examination motion picture 61 is divided for each frame. The examination frame image group 63 is transmitted to the trained second model 35. The examination motion picture 61 is received at the timing after the end of the endoscopy, but a video signal may be framed and processed in real time during the endoscopy before the examination motion picture 61 is created.

As shown in FIG. 12, the region of interest R is detected in response to the input of the examination frame image group 63 to the trained second model 35, and a detected image 64 is acquired. Since most of the examination frame images 62 not including the regions of interest R occupy the examination motion picture 61, a small number of detected images 64 including the regions of interest R is detected with respect to the number of input images. It is preferable that the detected images 64, which are detected, are temporarily stored in the storage memory 24, are displayed on the display 14 through the display controller 22, and are confirmed by the user. Alternatively, the detected images 64 may be stored in the database 12 instead of being temporarily stored in the storage memory 24. It is preferable to delete the examination frame image 62 in which the region of interest R is not detected, through the input, unless otherwise specified.

Figure 13:
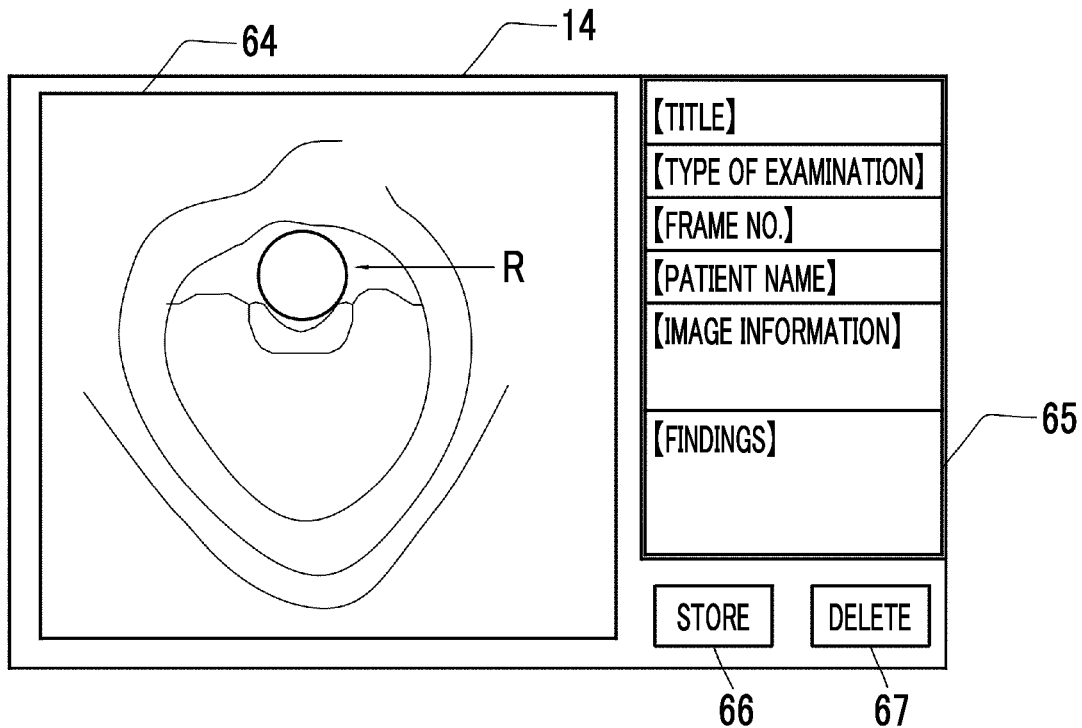
FIG. 13 is a diagram illustrating display of a detected image detected by the second model on a display.

As shown in FIG. 13, the user can individually perform a diagnosis with respect to the detected image 64 displayed on the display 14. The user can confirm image information displayed in the region of interest R or an image information display field 65, and can input a title or findings. Further, the user may select a store button 66 after the diagnosis to store the detected image 64 in the database 12 or may select a delete button 67 to delete the detected image 64 in a case where the detected image 64 is not necessary.

Figure 14:
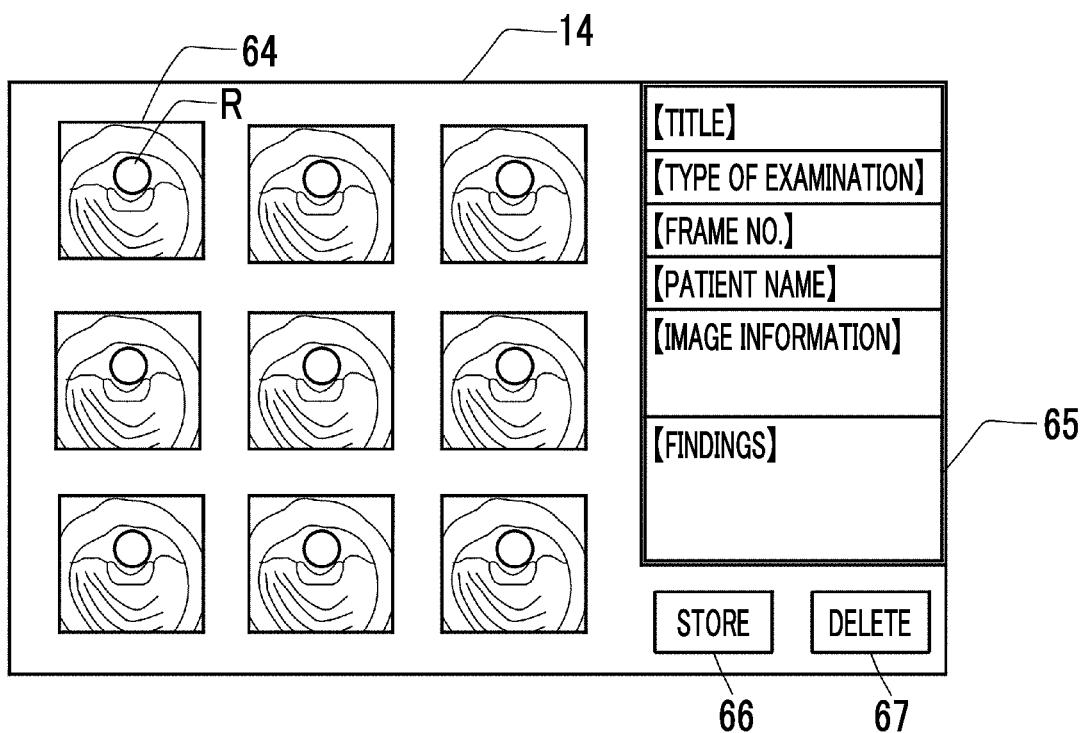
FIG. 14 is a diagram illustrating display of thumbnails of the detected images.

As shown in FIG. 14, the thumbnails of the detected images 64 may be displayed and used for the diagnosis. In that case, it is preferable to be able to perform the selection of the detected image 64 by which information is displayed in the image information display field, through the operation of a cursor or a keyboard. Further, the store button 66 or the delete button 67 may be operated collectively for the plurality of detected images 64.

In a case where the video signal is framed and region-of-interest detection processing is performed in real time during the endoscopy, the examination frame images 62 created by framing the video signal are appropriately transmitted to the trained second model 35 from the endoscope system 13. The trained second model 35 performs detection processing of the region of interest R each time the examination frame image 62 is received, and causes the display 14 to display the detected image 64 detected to have the region of interest R. The detected image 64 displayed on the display 14 including thumbnail display can be used for the user to perform a diagnosis as in a case of being acquired after the end of the examination, and can be stored and deleted.

Figure 15:
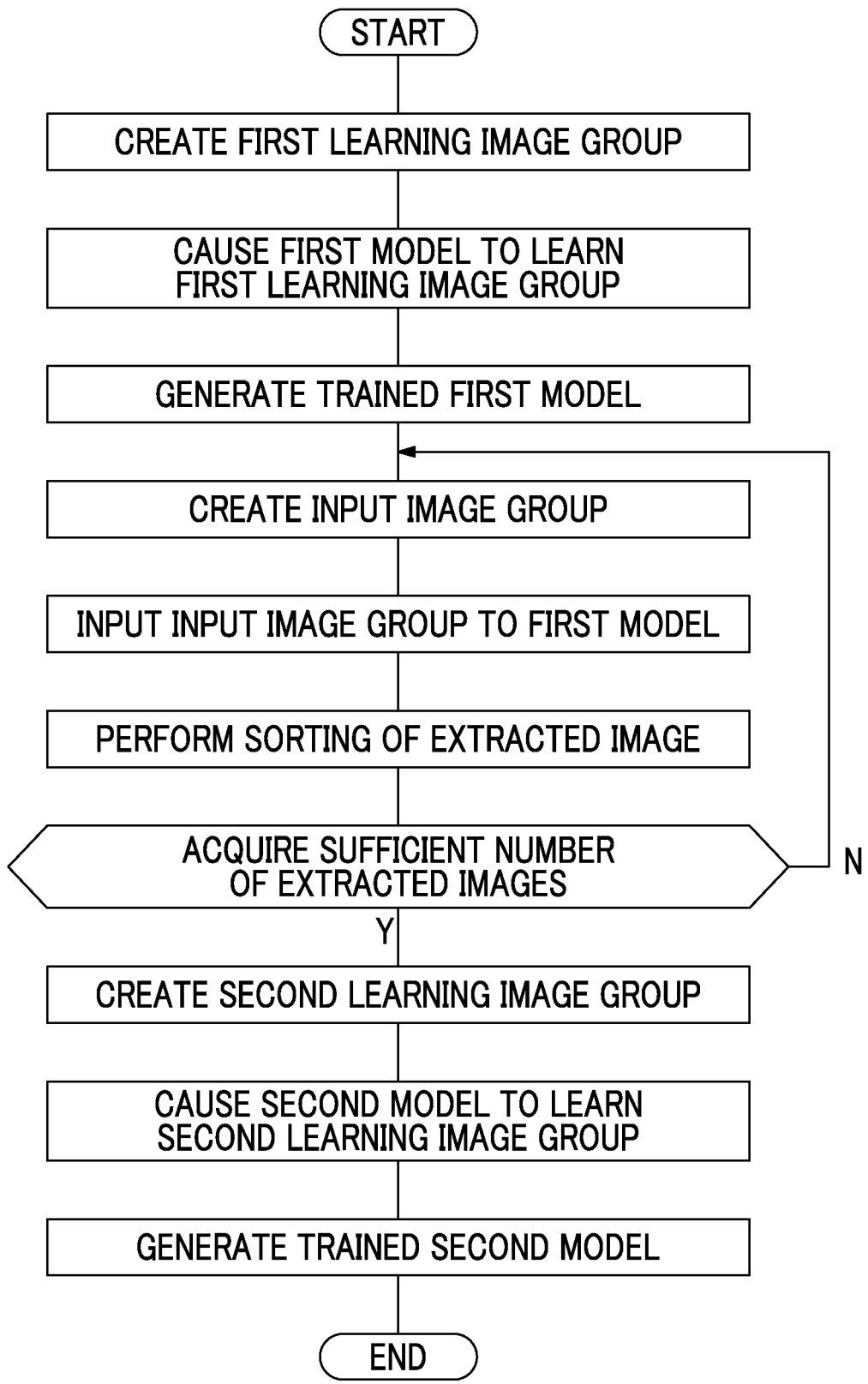
FIG. 15 is a flowchart for generation of the trained second model.

As shown in FIG. 15, a flowchart up to the generation of the trained second model 35 that detects the region of interest R will be described. The first model 33 learns the first learning image group 44 consisting of the normal image 42 having no region of interest R, and the trained first model 33 is generated. The trained first model 33 performs the abnormality detection for determining whether the input image is positive or negative on the basis of the content of the first learning. The sorting for acquiring the extracted image by using the result of the abnormality detection is performed. The sorting includes the first sorting and the second sorting, and at least one of the first sorting or the second sorting is performed. In the first sorting, the non-extracted normal image 47 and the extracted normal image 48 are sorted in response to the input of the first input image group 46, and the first sorting is repeated until a sufficient number of extracted normal images 48 are obtained. Further, in the second sorting, the non-extracted abnormal image 51 and the extracted abnormal image 50 are sorted in response to the input of the second input image group 49, and the second sorting is repeated until a sufficient number of extracted abnormal images 50 are obtained. The second learning image group 52 having the extracted normal image 48 and the extracted abnormal image 50, which are acquired through the sorting, and the normal image 42 and the abnormal image 43, which are not at least for preventing erroneous recognition in the abnormality detection, is created. The second model learns the second learning image group, and the trained second model 35 that detects the examination frame image 62 having the region of interest R is generated.

In a case where the examination frame image group 63 of the acquired examination motion picture 61 is input to the generated trained second model 35, the detected image 64 having the region of interest R is detected from a large number of frame images and is temporarily stored. The detected image 64 is temporarily stored and then is displayed on the display 14, and can be used for the user to perform a diagnosis. The user can input and store the image name and findings through the diagnosis.

The learning method of the first model will be described. The learning method includes learning of an autoencoder, learning of a GAN, learning of image interpolation, and the like. The GAN is also called a generative adversarial network, generates a non-existent image by using a discriminator and a generator, and has two patterns, that is, abnormality detection using the discriminator and abnormality detection using the generator in a case of using the abnormality detection. Abnormality detection using a combination of the discriminator and the generator may be performed.

The first model 33 learns the first learning image group through the first learning to generate an autoencoder. The first model 33 also calculates a reference intermediate feature amount, which serves as a reference, in the normal image 42 through the first learning. The autoencoder performs autoencoding in which each image of the input image group input in the abnormality detection is encoded and an intermediate feature amount is calculated and then the calculated intermediate feature amount is decoded on the basis of the content of the first learning and an autoencoded image is generated. The abnormality detection is performed by using at least one of the value of a restoration error, which is the difference calculated by comparing the image before the autoencoding and the image after the autoencoding, or a comparison result such as the difference between the distributions of the intermediate feature amount of the input medical image and the reference intermediate feature amount. A case where the value of the restoration error or the value of the comparison result such as the difference between the distributions exceeds a preset threshold value is determined to be abnormal, and a case where the value of the restoration error or the value of the comparison result such as the difference between the distributions does not exceed the threshold value is determined to be normal.

The first model 33 learns the first learning image group through the first learning to generate a discriminator of the GAN. The parameters of the discriminator are fixed, intermediate feature amount distribution of the discriminator in a case where first learning data is input is calculated, and the above intermediate feature amount distribution is compared with an intermediate feature amount in a case where an input image is input to the discriminator, whereby the abnormality detection is performed. The input image is determined to be abnormal in a case where the difference calculated by the comparison exceeds a preset threshold value, and the input image is determined to be normal in a case where the difference calculated by the comparison does not exceed the preset threshold value.

The first model 33 learns the first learning image group through the first learning to generate a generator of the GAN. The parameters of the generator are fixed, and noise input to the generator is optimized so that the difference between the input image and a generated image of the generator is small. The first model 33 performs the abnormality detection by comparing the optimized generated image with the input image. A case where the difference calculated by the comparison exceeds a preset threshold value is determined to be abnormal, and a case where the difference calculated by the comparison does not exceed the preset threshold value is determined to be normal.

The first model 33 learns the first learning image group through the first learning to generate an image interpolator. The image interpolator randomly makes a region in the image deficient for the normal image 42 and makes a region corresponding to the region of interest R deficient for the abnormal image 43, in each medical image constituting the input image group, which has been input. The image interpolator interpolates the deficient part of the medical image, which has been made deficient, on the basis of the reference calculated in the first learning, and acquires an interpolated image. The first model 33 calculates a restoration error by comparing the image before the deficiency with the image after the interpolation, for each medical image, and performs the abnormality detection. A case where the restoration error exceeds a preset threshold value is determined to be abnormal, and a case where the restoration error does not exceed the preset threshold value is determined to be normal.

In the present embodiment, the medical image learning method has been described with an example in which the medical image processing device 11 is connected to the endoscope system 13 and the examination motion picture acquired by the endoscopy is processed, but the present invention is not limited thereto, and the trained model may be generated for a motion picture or a frame image group acquired by another medical device, such as an ultrasonic image capturing device or a radiography device. Further, the trained model may be generated by using a device having a function different from that of the medical image processing device 11.

In each embodiment, the hardware structures of processing units that execute various kinds of processing, such as the central controller 20, the image processing unit 21, the display controller 22, the input reception unit 23, the storage memory 24, and the trained model management unit 30, are various processors to be described below. The various processors include, for example, a programmable logic device (PLD) that is a processor having a changeable circuit configuration after manufacture, such as a field programmable gate array (FPGA), and a dedicated electrical circuit that is a processor having a dedicated circuit configuration designed to perform various processing, in addition to the central processing unit (CPU) that is a general-purpose processor which executes software (program) to function as various processing units.

One processing unit may be constituted of one of the various processors or may be constituted of a combination of two or more processors of the same type or different types (for example, a combination of a plurality of FPGAs and a combination of a CPU and an FPGA). Alternatively, the plurality of processing units may constitute one processor. A first example in which the plurality of processing units constitute one processor is an aspect in which one or more CPUs and software are combined to constitute one processor and the processor functions as the plurality of processing units, as typified by a computer such as a client and a server. A second example is an aspect in which a processor that realizes all the functions of a system including the plurality of processing units with one integrated circuit (IC) chip is used, as typified by a system on chip (SoC) or the like. As described above, various processing units are constituted of one or more of the above-described various processors as hardware structures.

Furthermore, more specifically, electric circuitry in which circuit elements, such as semiconductor elements, are combined is used as the hardware structures of these various processors. Further, a storage device, such as a hard disc drive (HDD) or a solid state drive (SSD), is used as the hardware structure of the storage unit.

EXPLANATION OF REFERENCES

10: medical image processing system
11: medical image processing device
12: database
13: endoscope system
13a: endoscope
14: display
15: user interface
20: central controller
21: image processing unit
22: display controller
23: input reception unit
24: storage memory
30: trained model management unit
31: first learning image group creation unit
32: input image group creation unit
33: first model
34: second learning image group creation unit
35: second model
41: stored image group
42: normal image
43: abnormal image
44: first learning image group
45: confirmation image group
46: first input image group
47: non-extracted normal image
48: extracted normal image
49: second input image group
50: extracted abnormal image
51: non-extracted abnormal image
52: second learning image group
61: examination motion picture
62: examination frame image
63: examination frame image group 64: detected image
65: image information display field
66: store button
67: delete button
R: region of interest
T: treated mark

What is claimed is:

1. A medical image learning method comprising:
generating a first model through first learning using a first learning image group including a normal image which is a medical image having no region of interest;
inputting an input image group to the first model, the input image group including at least a medical image different from the first learning image group, to perform abnormality detection based on a difference from a reference of the first model;
performing sorting of an extracted image from the input image group, the extracted image being used for learning to prevent erroneous recognition of the region of interest, according to a result of the abnormality detection; and
generating a second model through second learning using a second learning image group including at least the extracted image, the second model detecting a medical image having the region of interest from input medical images.

2. The medical image learning method according to claim 1,
wherein each medical image of the input first learning image group is generated or restored in the first learning.

3. The medical image learning method according to claim 1, wherein
the input image group includes the normal image, and
the sorting is a first sorting where the medical image determined to be abnormal as the result of the abnormality detection is sorted into the extracted image.

4. The medical image learning method according to claim 1, wherein
the input image group includes an abnormal image which is a medical image having the region of interest, and
the sorting is a second sorting where the medical image determined to be normal as the result of the abnormality detection is sorted into the extracted image.

5. The medical image learning method according to claim 1, wherein
there are a case where the input image group includes the normal image and a case where the input image group includes an abnormal image which is a medical image having the region of interest,
in the case where the input image group includes the normal image, the sorting is a first sorting where the medical image determined to be abnormal as the result of the abnormality detection is sorted into the extracted image,
in the case where the input image group includes the abnormal image, the sorting is a second sorting where the medical image determined to be normal as the result of the abnormality detection is sorted into the extracted image, and
the first model switches between the first sorting and the second sorting depending on a type of the input image group.

6. The medical image learning method according to claim 1,
wherein the second learning image group includes the extracted image and an medical image different from the extracted image.

7. The medical image learning method according to claim 1,
wherein a degree of abnormality of each medical image of the input image group is evaluated through the abnormality detection, and
the second model is generated through the second learning using the second learning image group weighted on each medical image according to the degree of abnormality.

8. The medical image learning method according to claim 7,
wherein in the weighting,
weight is set small for the extracted image, and
weight is set large for a non-extracted image, which is not sorted as the extracted image from the input image group.

9. The medical image learning method according to claim 1,
wherein the first model is an autoencoder.

10. The medical image learning method according to claim 9,
wherein the first model learns autoencoding and calculates a reference intermediate feature amount of the normal image, in the first learning,
acquires an autoencoded image and an intermediate feature amount on the basis of each medical image of the input image group input to the first model, and
performs the abnormality detection by using at least one of a restoration error obtained by comparing an image before the autoencoding with the autoencoded image or a comparison result between the reference intermediate feature amount and the intermediate feature amount.

11. The medical image learning method according to claim 1,
wherein the first model is a GAN, and performs the abnormality detection by using at least one of a trained discriminator or a trained generator.

12. The medical image learning method according to claim 1,
wherein the first model learns image interpolation through the first learning,
makes each medical image constituting the input image group, which is input to the first model, deficient and interpolates the deficiency by using a reference calculated through the first learning, and
performs the abnormality detection by using a restoration error calculated by comparing the medical image before the deficiency with the medical image after the interpolation.

13. A medical image processing device comprising:
a processor configured to:
generate a first model through first learning using a first learning image group including a normal image which is a medical image having no region of interest;
input an input image group to the first model, the input image group including at least a medical image different from the first learning image group, to perform abnormality detection based on a difference from a reference of the first model;
perform sorting of an extracted image from the input image group, the extracted image being used for learning to prevent erroneous recognition of the region of interest, according to a result of the abnormality detection, and generate a second model through second learning using a second learning image group including at least the extracted image, the second model detecting a medical image having the region of interest from input medical images.

* * * * *